(12) United States Patent
Bartolome et al.

(10) Patent No.: US 9,354,186 B2
(45) Date of Patent: May 31, 2016

(54) X-RAY SENSOR AND SIGNAL PROCESSING ASSEMBLY FOR AN X-RAY COMPUTED TOMOGRAPHY MACHINE

(71) Applicant: Texas Instruments Incorporated, Dallas, TX (US)

(72) Inventors: Eduardo Bartolome, Dallas, TX (US); Sreenivasan K. Koduri, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 294 days.

(21) Appl. No.: 14/187,905

(22) Filed: Feb. 24, 2014

(65) Prior Publication Data

US 2014/0270057 A1    Sep. 18, 2014

Related U.S. Application Data

(60) Provisional application No. 61/780,434, filed on Mar. 13, 2013.

(51) Int. Cl.
| | |
|---|---|
| G01N 23/04 | (2006.01) |
| H01L 21/66 | (2006.01) |
| G01T 1/20 | (2006.01) |
| H01L 27/146 | (2006.01) |

(52) U.S. Cl.
CPC ............ *G01N 23/046* (2013.01); *G01T 1/2018* (2013.01); *H01L 22/10* (2013.01); *H01L 27/1469* (2013.01); *H01L 27/14661* (2013.01); *G01N 2223/419* (2013.01)

(58) Field of Classification Search
CPC combination set(s) only.
See application file for complete search history.

(56) References Cited

U.S. PATENT DOCUMENTS

| 5,841,310 | A | 11/1998 | Kalthoff et al. |
|---|---|---|---|
| 7,659,519 | B1 * | 2/2010 | Zheng .................. G01T 1/2018 250/370.11 |
| 2002/0070343 | A1 * | 6/2002 | Hoffman ............... G01T 1/2985 250/367 |
| 2010/0290199 | A1 * | 11/2010 | Schmid ................ B81C 1/0023 361/752 |
| 2011/0211319 | A1 * | 9/2011 | Kosowsky ........... H05K 1/0254 361/763 |
| 2012/0133001 | A1 * | 5/2012 | Tkaczyk ................ H01L 27/20 257/414 |

OTHER PUBLICATIONS

"64-Channel, Current-Input Analog-to-Digital Converter," SBAS368C—May 2006—Revised Jul. 2011, www.ti.com, 26 pagess.

* cited by examiner

*Primary Examiner* — Phillip A Johnston
*Assistant Examiner* — Hsien Tsai
(74) *Attorney, Agent, or Firm* — Steven A. Shaw; Frank D. Cimino

(57) ABSTRACT

An apparatus having an X-ray sensor assembly with X-ray blocking pixels divided by X-ray transmitting gaps with the X-ray blocking pixels casting an X-ray blocking shadow; and a die containing signal processing electronics, with the signal processing electronics positioned substantially entirely within the X-ray blocking shadow. A method for detecting the alignment between the X-ray sensor assembly and the die is disclosed. Also disclosed is an X-ray computed tomography machine having a printed circuit board ("PCB"), a die embedded in the PCB, and a signal source wherein signals are routed to and from the die by traces on at least one of the surfaces of the PCB.

20 Claims, 7 Drawing Sheets

X-RAY SENSOR AND SIGNAL PROCESSING ASSEMBLY FOR AN X-RAY COMPUTED TOMOGRAPHY MACHINE

This application claims priority from U.S. provisional patent application Ser. No. 61/780,434 filed Mar. 13, 2013 for MICROSIP PACKAGING SOLUTION FOR CT SCANNER of Eduardo Bartolome, which is hereby incorporated by reference for all that it discloses.

BACKGROUND

An X-ray computed tomography machine uses computer-processed x-rays to produce tomographic images of specific areas of a scanned object, allowing the user to see what is inside it without cutting it open. Medical imaging is the most common application of X-ray CT.

DETAILED DESCRIPTION

Figure 6:
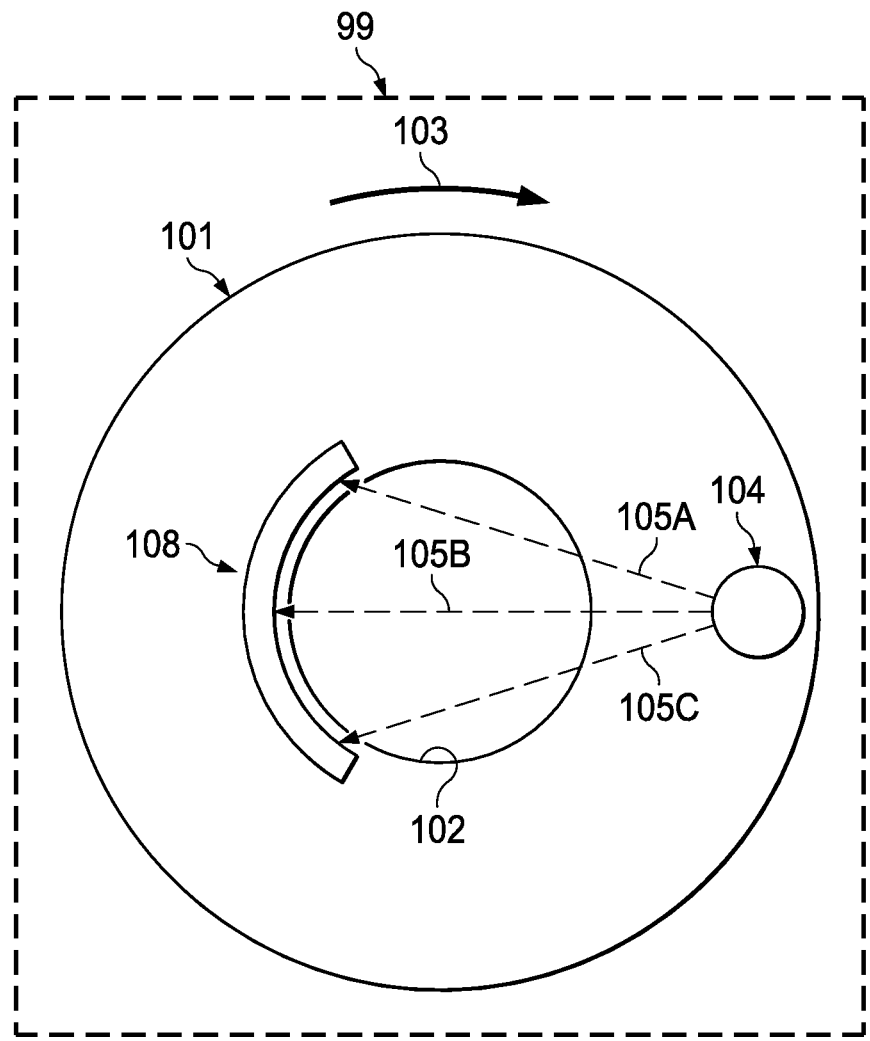
FIG. 6 is schematic end elevation view of a gantry of a CT machine having an X-ray sensor assembly and signal processing electronics as described in FIGS. 7-9.
Figure 7:
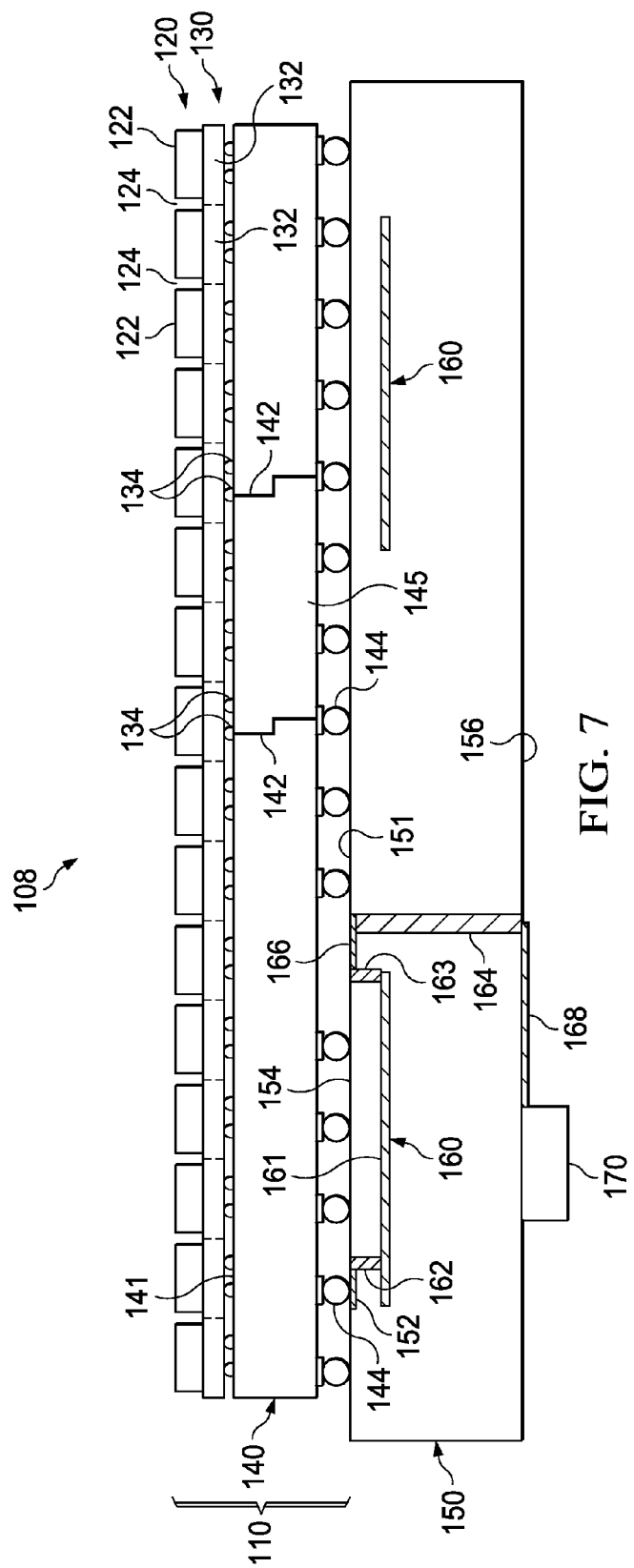
FIG. 7 is a schematic side elevation view of an X-ray sensor assembly mounted on a printed circuit board ("PCB") having an integrated circuit ("IC") die embedded therein.

This specification, in general, describes an X-ray computed tomography machine 99, FIG. 6, that includes an X-ray sensing and signal processing apparatus 108 that comprises an X-ray sensor assembly 110, FIG. 7, that is supported on a printed circuit board ("PCB") 150. An integrated circuit die 160 buried in the PCB 150 processes signals from the X-ray sensor assembly 110. Signals from the sensor assembly 110 are routed to the die 160 through traces 152 on the top surface 151 of the PCB 150 and then through micro-vias 162. Processed signals from the die 160 are routed back to the top surface of the PCB 150 through micro-vias 163 and traces 166 on the top surface 151 of the PCB 150 and then to through hole vias 164 (sometimes referred to as "hole vias" herein) extending through the PCB 150. Then the signals are routed from the through hole vias 164 and traces 168 on bottom surface 156 to other electrical circuitry 170 located on the bottom surface 156 of the PCB 150. A system for aligning the X-ray sensor assembly 110 with the IC die 160 to avoid exposing signal processing electronics within the die 160 to harmful X-rays, such as 105A, 105B, 105C shown in FIG. 6. The resulting structure is also described.

Figure 1:
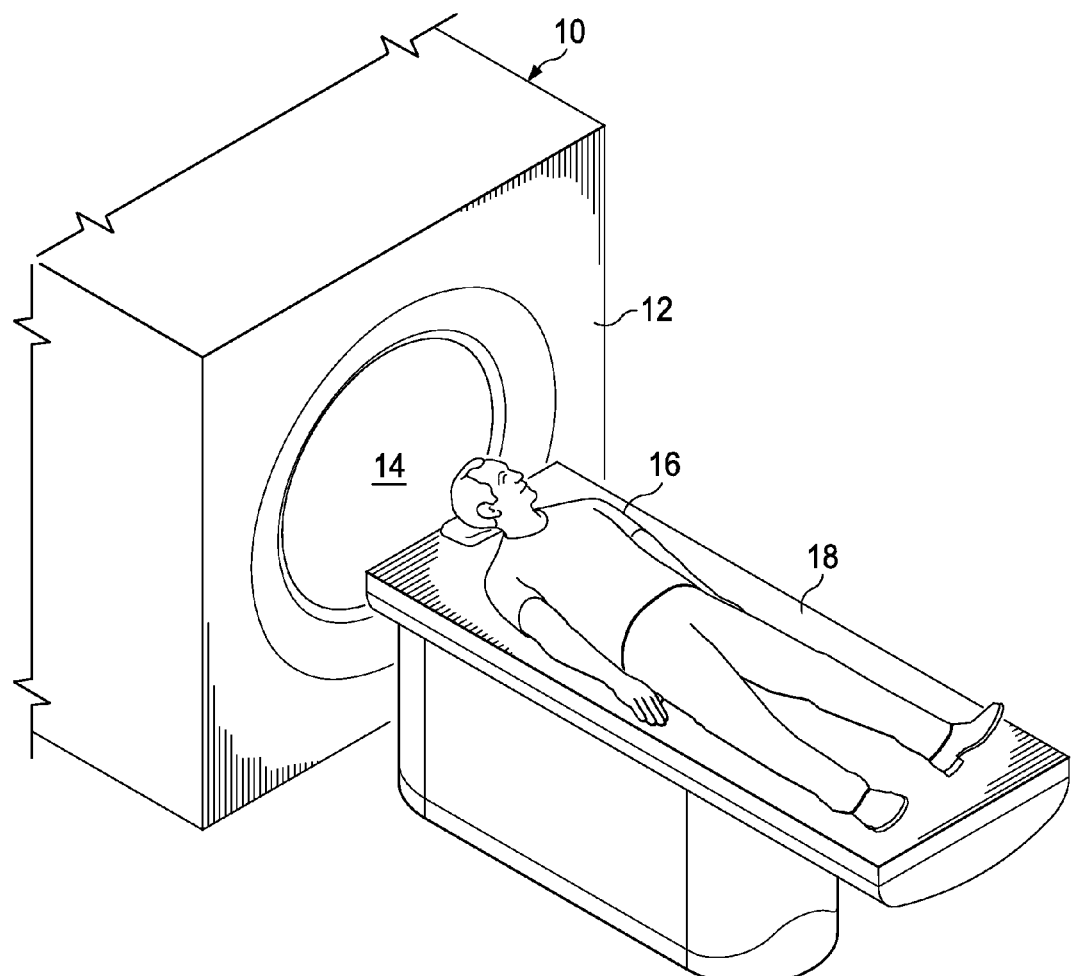
FIG. 1 is a perspective view of a prior art X-ray computed tomography machine ("CT machine").

FIG. 1 illustrates a prior art X-ray computed tomography machine 10 (CT machine 10). The CT machine 10 has a CT housing 12 with a center opening 14 therein. During CT operation, a patient 16 lies on a horizontally disposed table 18. The table 18 is slowly moved through the central opening 14 as X-rays from the machine pass through the patient's body.

Figure 2:
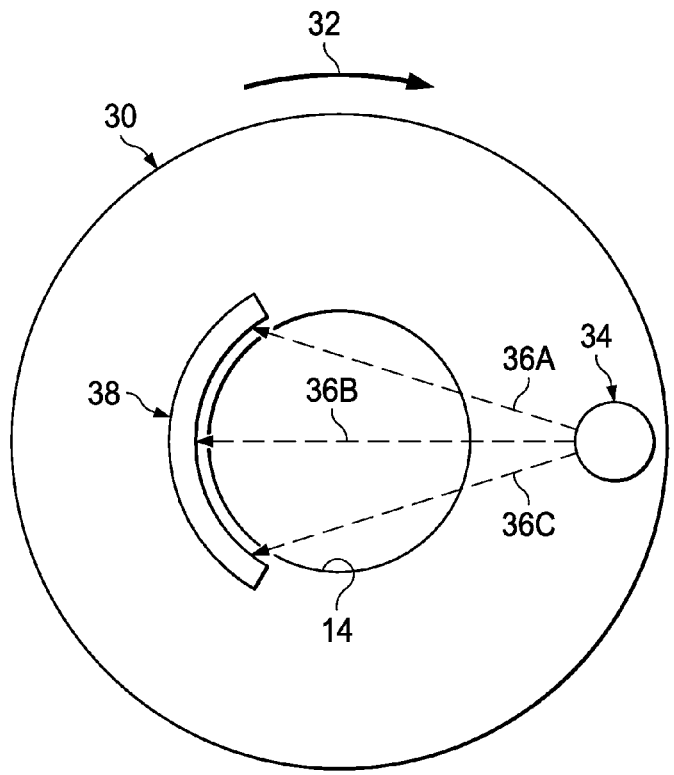
FIG. 2 is schematic end elevation view of a gantry of a prior art CT machine.

FIG. 2 is a cutaway schematic view of a gantry 30 of the prior art CT machine 10. The gantry 30 is a massive doughnut-shaped device that is positioned behind a front cover of the CT machine 10, FIG. 1. The gantry 30 rotates in direction 32 as the patient is moved through the opening 14. The gantry 30 includes an X-ray tube 34 positioned on one side of the central hole 14. An X-ray sensor assembly 38 is positioned on the opposite side of the center opening 14. X-rays 36A, 36B, 36C from the X-ray tube 34 are sensed by the sensor assembly 38. Analog signals from the sensor assembly 38 are processed and used to create three-dimensional images of the interior of the patient's body.

Figure 3:
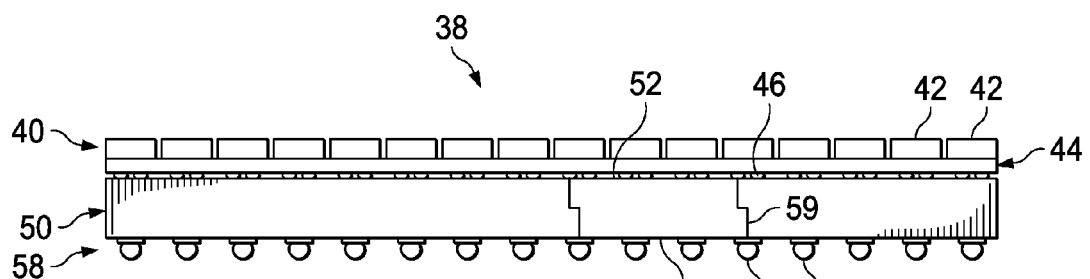
FIG. 3 is a schematic side elevation view of a prior art X-ray sensor assembly of a CT machine.
Figure 4:
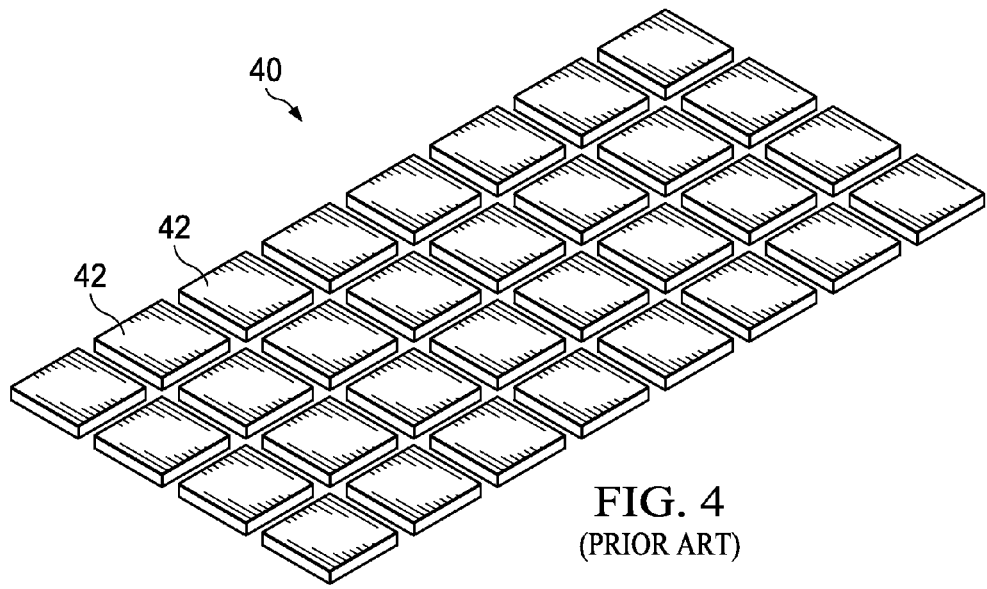
FIG. 4 is a schematic isometric view of a scintillator of a prior art X-ray sensor assembly.

FIG. 3 is a schematic side elevation view of a portion of the prior art X-ray sensor assembly 38. The sensor assembly 38 includes a scintillator array 40 mounted on a photo detector array 44 that is, in turn, mounted on a ceramic substrate 50. FIG. 4 is an enlarged isometric view of a top portion of the scintillator array 40, which comprises a grid of scintillator pixels 42. As shown by FIG. 3, the scintillator array 40 is supported on a photo detector array 44 having a plurality of pixels (not shown individually) corresponding to the pixels 42 of the scintillator array 40. (The term "pixel" as used herein may refer to an element of an image sensor as well as an element of an image.) The scintillator and photo detector pixels need to be held with high levels of geometric tolerances against mechanical, thermal, gravitational, and aging effects. Typically, a thick ceramic substrate 50 is used to provide the necessary support. The ceramic substrate 50 has flat upper and lower surfaces 52, 54. A plurality of conductor pads (not shown) are provided on the top surface 52 of substrate 50 in alignment with conductors 46 on the photo detector assembly 44. Electrical contacts such as balls 56 of a ball grid array 58 are provided on the bottom surface 54 of the ceramic substrate 50. Conductors 59 extending through vias in the substrate 50 and connect conductor pads (not shown) on the top surface 52 to corresponding ball conductors 56 on the bottom surface 54.

Figure 5:
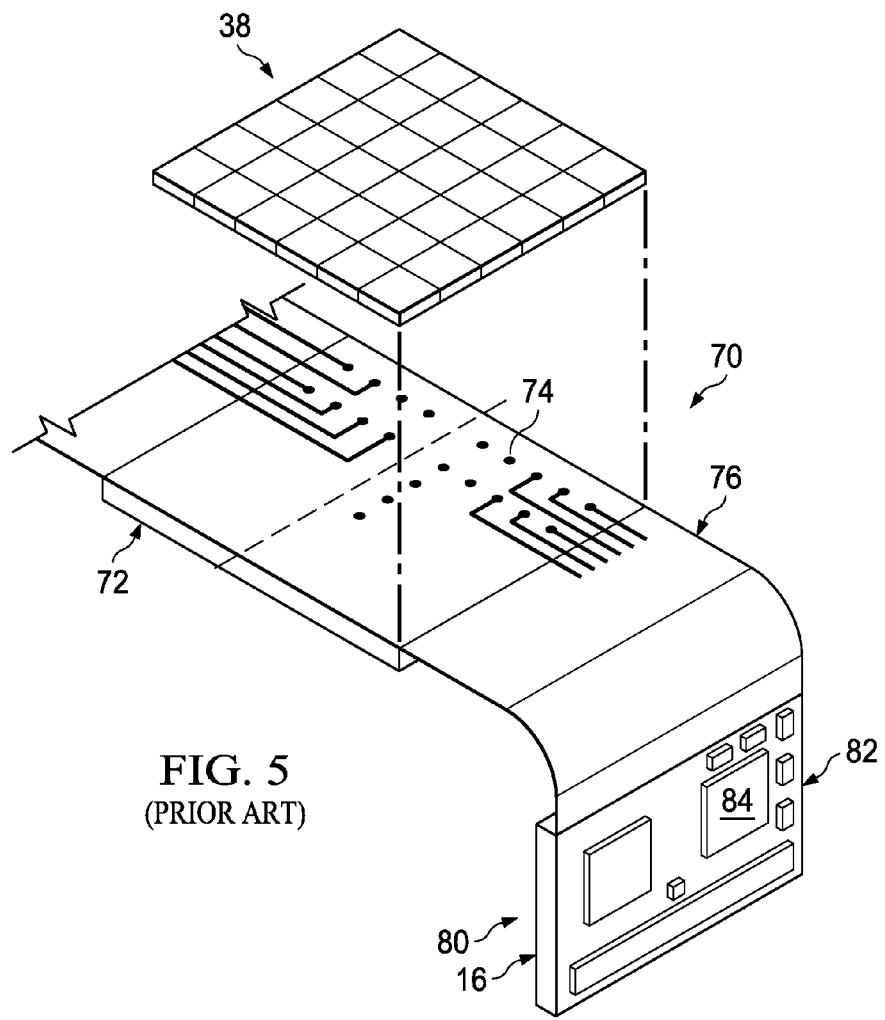
FIG. 5 is an isometric view showing the relationship between a prior art X-ray sensor assembly and signal processing electronics.

As illustrated by FIG. 5, the X-ray sensor assembly 38 is connected to signal processing electronics 80 which process analog signals from the photo detector array 44. The analog signals from the photo detector array 44 can be corrupted if transmitted over long distances. To avoid such signal corruption the analog signals would ideally be filtered and digitized by electronics in close proximity to the photo detector 44. The digital signals thus produced could then be safely transmitted, stored, and further processed with no loss of integrity.

Most X-rays that strike the scintillator array 40 are absorbed by it. However some amount of radiation may escape from the sensor assembly 38 due to gap's between scintillator pixels 42, or because some X-rays pass entirely through the sensor assembly 38. Such stray X-rays can significantly alter the characteristics of signal processing electronics placed in the proximity of the sensor assembly 38.

Various techniques have evolved to prevent damage to the signal processing electronics. Such techniques generally involve use of additional printed circuit boards (PCB's) to route the signals to signal processing electronics located a substantial distance away from the sensor assembly. An example of such a prior art assembly is shown in FIG. 5. An analog signal transfer assembly 70 transfers analog signals from the X-ray sensor assembly 38 to a signal processing assembly 80. The analog signal transfer assembly 70 includes a first conventional PCB 72. The ball grid array 58, FIG. 3, on the ceramic substrate 50 is placed in electrical contact with a corresponding conductor array on the conventional PCB 72. A flexible PCB 76 connects the first conventional PCB 72 to a second conventional PCB 82 having analog signal processing electronics mounted on it. A portion of the flexible PCB 76 and the second conventional PCB 82 extend generally perpendicular to the first conventional PCB 72 and parallel to the direction of X-rays from the X-ray tube 34. Although this structure places the signal processing electronics 82 at a distance from the source of the X-rays it has a number of drawbacks. Such structure undesirably increases the distance that the analog signals must travel to reach the signal processing electronics. Such structure also adds undesirable stack height (radial height) and mass to the entire X-ray sensor/signal processing assembly.

FIG. 6 illustrates a CT machine 99 having a gantry 101 with a central opening 102. The gantry 101 rotates in direction 103. An X-ray tube 104 is positioned on one side of the opening 102. An X-ray sensing and signal processing apparatus 108 is positioned on the other side of the opening 102. X-rays 105A, 105B, and 105C from the X-ray tube 104 travel through the opening 102, and any X-ray penetrable object therein, and strike the X-ray sensing and signal processing apparatus 108, described in detail below.

FIG. 7 is a side elevation view of the X-ray sensing and signal processing apparatus 108 of FIG. 6. The apparatus 108 comprises an X-ray sensor assembly 110 that in this embodiment includes a scintillator assembly 120. Scintillator assembly 120 has a plurality of scintillator pixels 122 separated by scintillator pixel gaps 124. A photo detector assembly 130, having a plurality of photo detector pixels 132, is positioned immediately below the scintillator assembly 120. Photo detector pixels 132 correspond to the scintillator pixels 122 positioned immediately above them. The photo detector 130 may be mounted on a ceramic substrate 140. Photo detector signal output contacts 134 engage corresponding contacts (not shown) on a top surface 141 of the ceramic substrate 140. Conductor filled vias 142 connect the contacts on the top of the ceramic substrate 140 with ball grid contacts 144 on the bottom surface 145 of the ceramic substrate 140. The ball contacts 144 on the bottom surface of the ceramic substrate 140 engage corresponding contacts 152, which may be signal traces, on the top surface 151 of a printed circuit board ("PCB") 150.

The PCB 150 has a plurality of integrated circuit ("IC") dies 160 buried below the surface 151 of the PCB 150. The IC dies 160 may each be buried at the same depth and may be laterally spaced apart a predetermined distance. Traces 152 on the top surface 151 of the PCB 150 connect the ceramic substrate ball contacts 144 to micro-vias 162 extending from the PCB top surface 151 to contacts on the top surface 161 of a buried die 160. Analog sensor signals from the X-ray sensor assembly 110 are input to die signal processing electronics through a set of traces 152 and a set of micro-vias 162. Other micro-vias 163 connect another set of contacts on the top surface 161 of the die 160 to a second set of surface traces 166 on the top surface 151 of the PCB 150. Processed sensor signals are thus transmitted from the dies 160 through micro-vias 163 and traces 166. Traces 166 are connected to hole vias 164 that extend from the top surface 151 of the PCB 150 to bottom surface 156 of the PCB 150. The processed sensor signals are thus transmitted to the bottom surface 156 of the PCB 150. Other signals such as power and control signals may also be routed from the die 160 to the bottom surface 156 of the PCB 150 by micro-vias 163, traces 166 and through hole vias 164. Other circuitry 170, such as passive circuit devices, power distribution lines, decoupling capacitors, and connectors to other circuits, are mounted on the bottom surface 156 of the PCB 150. The hole vias 164 may be connected to the other circuitry 170 by bottom surface traces 168. Thus, the circuitry connecting the IC dies 160 to the X-ray sensor 110 and to other circuit devices 170 may be located on the PCB top surface 151 or bottom surface 156. In one embodiment, all traces carrying signals to and from the die 160 are on the top and bottom surfaces 151, 156 of the PCB 150. In another embodiment a substantial portion of those traces are located on internal layers (not shown) of the PCB 150, as well as on the top and bottom surfaces 151, 156, with routing between layers provided by vias.

Figure 8:
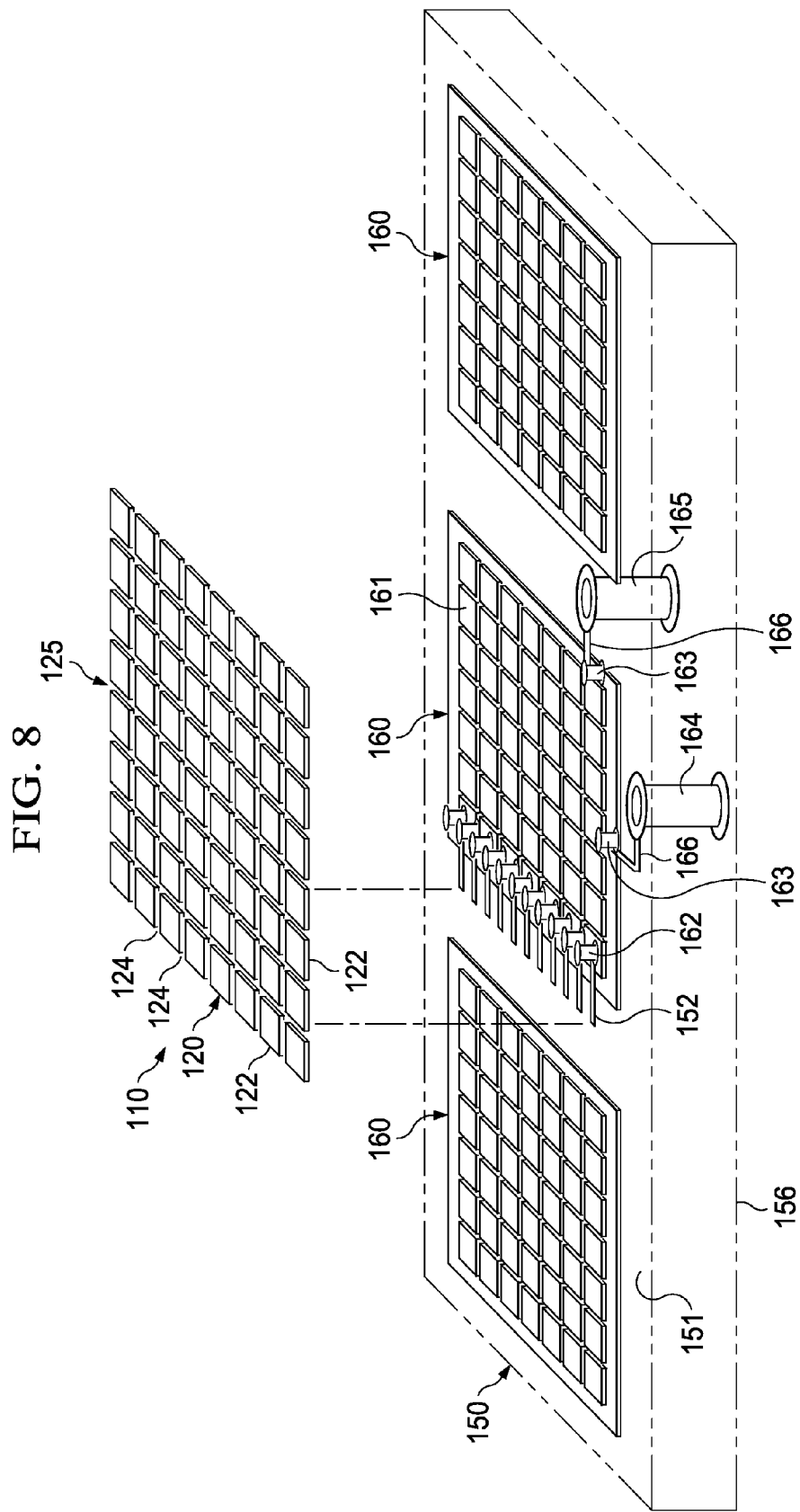
FIG. 8 is an exploded, partially transparent top view of an X-ray sensor assembly and a printed circuit board ("PCB") having an IC die embedded therein.
Figure 9:
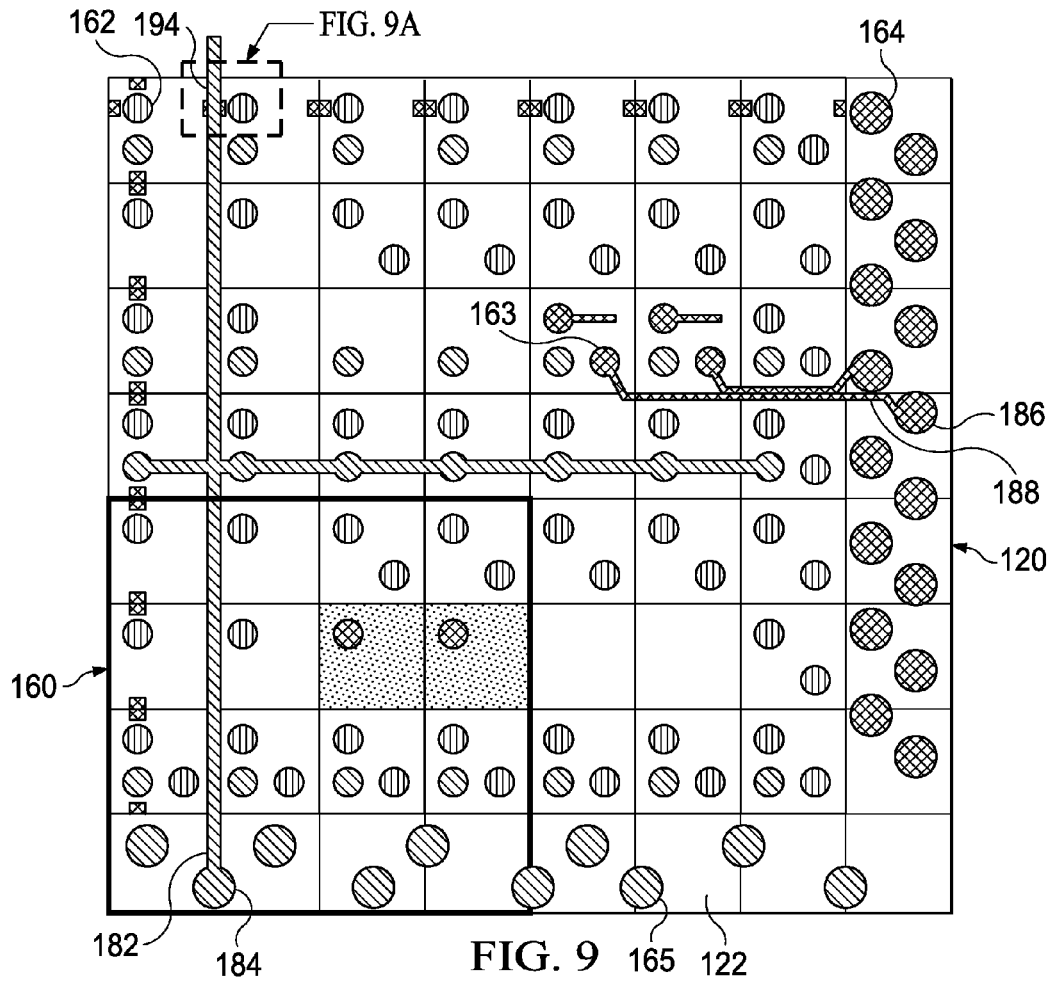
FIG. 9 is a detail view of the PCB and the embedded IC die of FIGS. 7 and 8 showing a projection of a scintillator portion of the X-ray sensor assembly thereon.

The above described X-ray sensing and signal processing apparatus 108 is shown in a schematic, transparent three-dimensional representation in FIG. 8. FIG. 9 is a top plan view of the die 160, which shows the position of the overlying scintillator pixels 122, various micro-vias 162, 163, and through hole vias 164 for control circuits and through-hole vias 165 for supply and reference circuits. In the embodiment shown in FIGS. 8 and 9 the top surface 161 of each die 160 is divided into a 7×7 unit grid, which underlies an 8×8 pixel grid of the scintillator 130, FIG. 7. The individual pixels 122 of the scintillator assembly 120 prevent radiation impinging thereon from passing through to the underlying die 160. However, the gaps 124 between scintillator pixels 122 do not block radiation. In the assembly shown in FIG. 9, the electronics inside the IC die 160 are all located in areas shaded from X-rays by scintillator pixels 122. The dies 160 are constructed and arranged such that the areas of the dies 160 that are exposed to radiation passing through the scintillator gaps 124 do not contain electronics. However, such gap projection areas, e.g. 194, may be used for purposes other than signal processing, such as for signal routing.

Figure 9A:
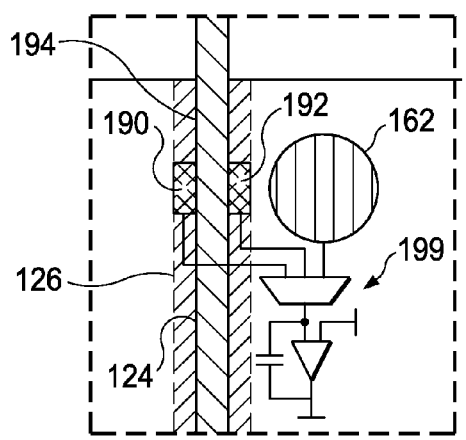
FIG. 9A is a detail view of a portion of FIG. 9.

A blowup of one of these gap projection lines 194 on the die 160 is shown in FIG. 9A. In one embodiment, a diode 190, 192 is positioned on each side of the gap projection line 194. One or both of the diodes 190, 192 will receive radiation if the gap projection line 194 is not properly aligned with the actual overlying scintillator pixel gap grid 125, FIG. 8. As shown by FIG. 9A, the same signal processing electronics 199 that are used to process an X-ray sensor signal may also be used to process a signal from an associated diode, e.g., 192. Signals from the various diodes 190,192, etc., may be processed to determine the misalignment between the underlying die 160 and the scintillator assembly 120. In one embodiment, this misalignment detection is used in association with a displacement assembly (not shown) during assembly to align the scintillator assembly 120 with the respective dies 160. In another embodiment, this misalignment detection is used after assembly for quality control purposes.

The circuitry and method used for processing signals from the X-ray sensor assembly 110, FIG. 7, may be the same or similar to that described in U.S. Pat. No. 5,841,310, issued Nov. 24, 1998 for CURRENT-TO-VOLTAGE INTEGRATOR FOR ANALOG-TO-DIGITAL CONVERTER, AND METHOD, and "64 Channel Current-Input Analog-to-Digital Converter Check of DDC264, SBAS 368C," May 2006, Revised July, 2011, which are both hereby incorporated by reference for all that is contained therein. The signal processing electronics in the dies 160 that are used to process signals from the X-ray sensor assembly 110, may also be used to process the alignment signals from gap sensing diodes 190, 192 of FIG. 9A, as mentioned above.

In the illustrated embodiments, the scintillator assembly 120, FIG. 7, has an 8×8 pixel array, which is projected onto a 7×7 unit grid of an integrated circuit die 160 and which overlaps it by one row and one column. It will be understood that all 64 pixels of the scintillator assembly 120 have signal inputs to the 7×7 unit IC die 160. Thus, there is not a 1 to 1 correspondence between the scintillator pixels 122 and the units of the die, even though all of the signals from the scintillator pixels are processed by electronics in the die 160.

Although certain specific embodiments of an X-ray computed tomography machine ("CT machine") and an X-ray sensing and signal processing apparatus and an alignment system therefor have been described in detail above, it will be understood by those skilled in the art after reading this disclosure that the specifically described devices and methods could be variously otherwise embodied. For example, although the embodiment of a CT machine that is specifically described herein is a medical CT machine, the CT machine features described herein are also applicable to other types of CT machines such as industrial CT machines used for imaging solder joints on printed circuit boards.

As another example, the X-ray sensing assembly 110, FIG. 7, which in the illustrated embodiment comprises a scintillator and photo detector array, may be otherwise embodied. For example, it may be a unitary sensing device that converts X-ray strikes directly into electrical signals. Such devices may use detectors based on compound semiconductors such as CDZnTe or the like. In some such devices the entire device acts as an X-ray shield, i.e. there are no gaps through which X-rays may pass. Thus, with such X-ray sensing assemblies there is no need for die and pixel gap alignment. However, the above described method and structure for signal routing on the surfaces of the PCB 150 rather than the die 160 remain applicable. Such signal routing could also be used with other imaging assemblies or in other assemblies where signal routing on the surface of a die is problematic.

The appended claims are intended to cover such alternative embodiments, except to the extent limited by the prior art.

What is claimed is:

1. An apparatus comprising:
    an X-ray sensor assembly with X-ray blocking pixels divided by X-ray transmitting gaps, said X-ray blocking pixels casting an X-ray blocking shadow; and
    a die containing signal processing electronics, said signal processing electronics being positioned substantially entirely within said X-ray blocking shadow.

2. The apparatus of claim 1, wherein said apparatus is an X-ray computed tomography machine ("CT machine") and further comprising an X-ray source; and
    wherein said X-ray blocking pixels comprise a first side exposed to said X-rays and an opposite second side, said second side having a plurality of contact surfaces that transmit electrical signals indicative of said X-rays impinged on said first side and wherein said X-ray blocking pixels are arranged in a X-ray blocking pixel grid by said gaps positioned therebetween; and further comprising:
    a printed circuit board ("PCB") having a first surface and an opposite second surface;
    wherein said die is buried in said PCB, said die having a first surface located proximate said first surface of said PCB and a second surface located proximate said second surface of said PCB, said die being spatially divided into a plurality of shaded die units by a die grid formed by projecting said X-ray blocking pixel grid onto said first surface of said die with said die grid corresponding to said X-ray transmitting gaps.

3. The CT machine of claim 2, further comprising:
    a first plurality of contact surfaces on said first surface of said die;
    a first plurality of vias extending between said first surface of said PCB and said first plurality of contact surfaces on said first surface of said die; and
    a first plurality of traces on said first surface of said PCB connecting said contact surfaces on the second side of said X-ray sensor assembly with said first plurality of vias.

4. The CT machine of claim 3 further comprising:
    a second plurality of contact surfaces on said first surface of said die;
    a second plurality of vias extending between said contact surfaces on said first surface of said die and said first surface of said PCB;
    a plurality of through hole vias extending between said first and second surfaces of said PCB;
    electrical circuitry on said second side of said PCB;
    a second plurality of traces on said first surface of said PCB connecting said second plurality of vias to said plurality of through hole vias; and
    a plurality of traces on said second side of said PCB connecting said plurality of through hole vias to said electrical circuitry on said second side of said PCB.

5. The CT machine of claim 2 further comprising an alignment detector adapted to sense misalignment between said X-ray sensor assembly and said die.

6. The CT machine of claim 5 wherein said die grid comprises a plurality of straight lines and wherein said alignment detector comprises at least one pair of diodes including a first diode positioned on one side of one of said plurality of straight lines and a second diode positioned on the other side of said one straight line.

7. The CT machine of claim 2, said X-ray sensor assembly comprising: a scintillator; a photodetector operably attached to the scintillator; and a ceramic substrate supporting the photodetector and mounted on the first surface of the PCB.

8. An X-ray computed tomography machine ("CT machine") comprising:
    a printed circuit board ("PCB") having opposite surfaces;
    a die embedded in the PCB; and
    a signal source; wherein signals from the signal source are routed to and from the die with traces on at least one of said opposite surfaces of the PCB.

9. The CT machine of claim 8 wherein:
    said PCB opposite surfaces comprise a first side and a second side;
    said die has a first side with a first plurality of surface contacts thereon positioned proximate said first side of said PCB and a second side positioned proximate said second side of said PCB;
    said signal source has a signal output side with a plurality of signal output contacts thereon positioned adjacent to said first side of said PCB;
    a first set of micro-vias extend from said first surface of said PCB to said first plurality of surface contacts on said die;
    a first set of traces on said first surface of said PCB connecting said signal output contacts on said signal source with said first set of micro-vias.

10. The CT machine of claim 9 wherein said first side of said die has a second set of contact surfaces thereon; and further comprising:
    a second set of micro-vias extending from said second set of contact surfaces on said first side of said die to said first side of said PCB;

a plurality of through hole vias extending between said first side and said second side of said PCB;

a second set of traces on said first side of said PCB connecting said second set of micro-vias to said plurality of through hole vias; and a set of traces on said second side of said PCB connecting said through hole vias to other electrical circuits.

11. A method of making an X-ray computed tomography machine ("CT machine") comprising:

providing a scintillator that projects a scintillator shadow with gaps therein; and positioning an integrated circuit die with image processing electronics thereof located substantially within the scintillator shadow and substantially outside of the gaps in the scintillator shadow.

12. The method of claim 11 further comprising sensing the alignment of the die relative to the scintillator.

13. The method of claim 11 wherein said sensing the alignment comprises using diodes positioned on opposite sides of one of the gaps in the scintillator shadow.

14. The method of claim 13 wherein said sensing the alignment is performed during the initial assembly of the CT machine.

15. The method of claim 13 wherein said sensing the alignment is performed after the CT machine is in use to determine whether the scintillator is still accurately aligned with the die.

16. The method of claim 11 further comprising burying the die in a PCB having a first surface positioned adjacent to the active surface of the die and routing X-ray sensor signals through traces on the first surface of the PCB and then through micro-vias in the PCB to contacts on the active surface of the die.

17. The method of claim 15 further comprising routing processed sensor signals from output contacts on the active surface of the die first to output micro-vias in the PCB that extend to the first surface of the PCB and then from the output micro-vias through traces on the first surface of the PCB to at least one through hole via extending from the first surface of the PCB to a second surface of the PCB opposite the first surface of the PCB.

18. The method of claim 17 further comprising routing the processed sensor signals to electrical circuits positioned on the second side of the PCB.

19. The method of claim 18 wherein routing the processed sensor signals to electrical circuits positioned on the second side of the PCB comprises routing the processed sensor signal through traces formed on the second surface of the PCB.

20. The method of claim 19 wherein routing the processed sensor signals to electrical circuits positioned on the second side of the PCB comprises routing the processed sensor signals to at least one of: power distribution lines, decoupling capacitors, and connectors to other circuits.

* * * * *